(12) United States Patent
Shin et al.

(10) Patent No.: US 11,967,680 B2
(45) Date of Patent: Apr. 23, 2024

(54) GEL POLYMER ELECTROLYTE COMPOSITION ATTAINING SHORTENED CROSSLINKING TIME, SECONDARY BATTERY COMPRISING SAME, AND MANUFACTURING METHOD FOR SECONDARY BATTERY

(71) Applicant: LG ENERGY SOLUTION, LTD., Seoul (KR)

(72) Inventors: Won Kyung Shin, Daejeon (KR); Won Tae Lee, Daejeon (KR); Young Ho Oh, Daejeon (KR); Chul Haeng Lee, Daejeon (KR); Kyoung Ho Ahn, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 0 days.

(21) Appl. No.: 18/286,747

(22) PCT Filed: Jan. 11, 2023

(86) PCT No.: PCT/KR2023/000478
§ 371 (c)(1),
(2) Date: Oct. 12, 2023

(87) PCT Pub. No.: WO2023/191270
PCT Pub. Date: Oct. 5, 2023

(65) Prior Publication Data
US 2024/0105990 A1 Mar. 28, 2024

(30) Foreign Application Priority Data
Mar. 31, 2022 (KR) .................. 10-2022-0040568

(51) Int. Cl.
*H01M 10/0525* (2010.01)
*C07C 69/96* (2006.01)
(Continued)

(52) U.S. Cl.
CPC ......... *H01M 10/0565* (2013.01); *C07C 69/96* (2013.01); *H01M 10/052* (2013.01);
(Continued)

(58) Field of Classification Search
CPC .......... H01M 10/0565; H01M 10/052; H01M 10/058; H01M 50/105; H01M 50/609;
(Continued)

(56) References Cited

U.S. PATENT DOCUMENTS

2003/0180623 A1* 9/2003 Yun .................. H01M 10/0565
429/316
2009/0317723 A1 12/2009 Yu et al.
(Continued)

FOREIGN PATENT DOCUMENTS

CN 112321827 * 2/2021
JP 2008-159496 A 7/2008
(Continued)

OTHER PUBLICATIONS

International Search Report and Written Opinion (with translation) dated Apr. 19, 2023 issued in corresponding International Patent Application No. PCT/KR2023/000478.
(Continued)

*Primary Examiner* — Lisa S Park
(74) *Attorney, Agent, or Firm* — Morgan, Lewis & Bockius LLP

(57) ABSTRACT

A gel polymer electrolyte composition, a secondary battery including the same, and a manufacturing method of a secondary battery are disclosed. Advantages of the disclosed aspects include increasing process efficiency by reducing the curing time of a gel polymer electrolyte while preventing leakage of an electrolyte.

15 Claims, 1 Drawing Sheet

(51) Int. Cl.
*H01M 10/052* (2010.01)
*H01M 10/0565* (2010.01)
*H01M 10/058* (2010.01)
*H01M 50/105* (2021.01)
*H01M 50/609* (2021.01)

(52) U.S. Cl.
CPC ....... *H01M 10/058* (2013.01); *H01M 50/105* (2021.01); *H01M 50/609* (2021.01); *H01M 2300/0025* (2013.01); *H01M 2300/0085* (2013.01)

(58) Field of Classification Search
CPC .. H01M 2300/0025; H01M 2300/0085; C07C 69/96
See application file for complete search history.

(56) References Cited

U.S. PATENT DOCUMENTS

| | | |
|---|---|---|
| 2011/0052999 A1 | 3/2011 | Lee et al. |
| 2012/0009715 A1 | 1/2012 | Sim et al. |
| 2018/0323471 A1 | 11/2018 | Ahn et al. |
| 2020/0203762 A1* | 6/2020 | Park .................. C08L 69/00 |
| 2020/0220212 A1* | 7/2020 | Ahn .................. H01M 10/0565 |
| 2021/0210787 A1 | 7/2021 | Shin et al. |

FOREIGN PATENT DOCUMENTS

| | | |
|---|---|---|
| KR | 10-0236843 B1 | 1/2000 |
| KR | 10-0278539 B1 | 1/2001 |
| KR | 10-0522685 B1 | 10/2005 |
| KR | 2008-0022677 A | 3/2008 |
| KR | 2009-0079571 A | 7/2009 |
| KR | 10-2014-0008264 A | 1/2014 |
| KR | 10-1716799 B1 | 3/2017 |
| KR | 10-2019-0012123 A | 2/2019 |
| KR | 10-2020-0020234 A | 2/2020 |
| WO | 2011/115319 A1 | 9/2011 |

OTHER PUBLICATIONS

He, "Effects of gelation behavior of PPC-based electrolyte on electrochemical performance of solid state lithium battery", SN Applied Sciences, vol. 1, No. 3, Doc. No. 205, (Feb. 2, 2019) pp. 1-8.

Office Action dated Dec. 22, 2023 issued in counterpart Korean Patent Application No. 10-2022-0040568 with machine translation.

* cited by examiner

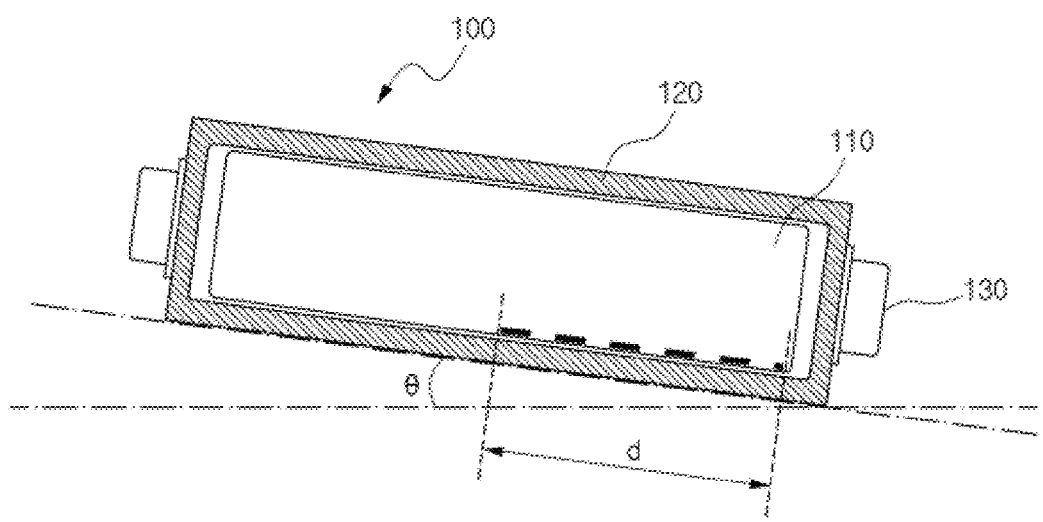

GEL POLYMER ELECTROLYTE COMPOSITION ATTAINING SHORTENED CROSSLINKING TIME, SECONDARY BATTERY COMPRISING SAME, AND MANUFACTURING METHOD FOR SECONDARY BATTERY

TECHNICAL FIELD

This application claims the benefit of priority based on Korean Patent Application No. 10-2022-0040568 filed on Mar. 31, 2022, and all contents disclosed in the literature of the Korean Patent Application are included as part of this specification.

The present invention relates to a gel polymer electrolyte composition with reduced crosslinking time, a secondary battery including the same, and a manufacturing method of a secondary battery.

BACKGROUND TECHNOLOGY OF THE INVENTION

Recently, secondary batteries capable of charging and discharging have been widely used as energy sources for wireless mobile devices. In addition, secondary batteries are attracting attention as an energy source for electric vehicles, hybrid electric vehicles, etc., which are being proposed as a solution to air pollution, such as existing gasoline vehicles and diesel vehicles using fossil fuels. Therefore, the types of applications using secondary batteries are becoming very diversified due to the advantages of secondary batteries, and it is expected that in the future, secondary batteries will be applied to more fields and products than they are now.

The secondary battery has a structure in which an electrode assembly is embedded in a battery case together with an electrolyte, and the electrode assembly is sufficiently impregnated and wetted with the electrolyte to exhibit electrical performance. However, electrolyte leakage occurs during the charging and discharging process, which causes defects in the battery cell and fire may further be generated.

As a method of preventing leakage of the electrolyte, a gel polymer electrolyte is being studied. However, the gel polymer electrolyte undergoes a cross-linking process after injecting the electrolyte into the battery. It takes a lot of time for electrolyte crosslinking, which causes a decrease in process efficiency and an increase in manufacturing cost.

Therefore, there is a need for a technology capable of reducing the curing time according to the crosslinking reaction in the electrolyte while introducing a gel polymer electrolyte to prevent leakage of the electrolyte.

DESCRIPTION OF THE INVENTION

Technical Problem

The present invention has been devised to solve the above problems, and is directed to provide a gel polymer electrolyte composition that can significantly reduce curing time compared to conventional ones, and a secondary battery including the same.

Technical Solution

The present invention provides a gel polymer electrolyte composition. In an exemplary embodiment, a gel polymer electrolyte composition according to the present invention includes: an oligomer represented by Formula 1 below; a curing accelerator that is a monocyclic or a polycyclic amine compound; a polymerization initiator; a non-aqueous solvent; and a lithium salt.

[Formula 1]

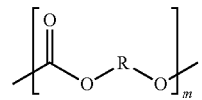

In Formula 1,

R is an alkylene having carbon numbers 1 to 5 substituted with an alkyl group having carbon numbers 1 to 5, and m is an integer from 1 to 50.

In an exemplary embodiment, the gel polymer electrolyte composition has a curing time in the range of 10 minutes to 50 minutes under a heat treatment condition of 55 to 80° C.

In a specific exemplary embodiment, the content of the oligomer is in the range of 0.1 to 30 parts by weight based on the total 100 parts by weight of the gel polymer electrolyte composition.

In another exemplary embodiment, the curing accelerator includes one or more among a pyrimidine-based, an imidazole-based, a purine based, a thiadiazole-based, and a pyrrole based curing accelerators.

In a specific exemplary embodiment, among the curing accelerators, the pyrimidine-based curing accelerator is one or more of the following formulas 1-a to 1-g.

[Formula 1-a]

[Formula 1-b]

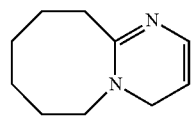

[Formula 1-c]

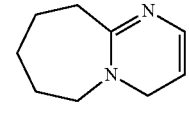

[Formula 1-d]

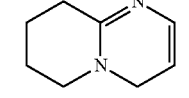

[Formula 1-e]

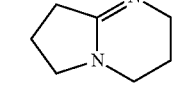

[Formula 1-f]

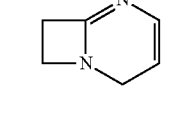

[Formula 1-g]

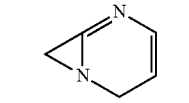

In a specific exemplary embodiment, among the curing accelerators, the imidazole-based curing accelerator is one or more of the following formulas 2-a to 2-i.

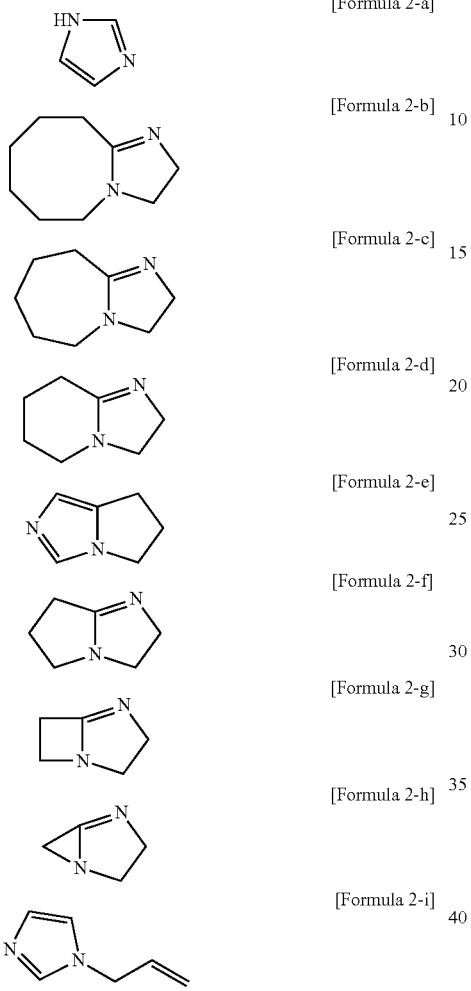

[Formula 2-a]

[Formula 2-b]

[Formula 2-c]

[Formula 2-d]

[Formula 2-e]

[Formula 2-f]

[Formula 2-g]

[Formula 2-h]

[Formula 2-i]

In a specific exemplary embodiment, among the curing accelerators, the purine-based curing accelerator is represented by the following formula 3-a.

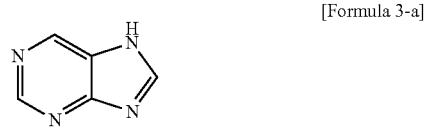

[Formula 3-a]

In a specific exemplary embodiment, among the curing accelerators the thiadiazole-based curing accelerator is one or more of the following formulas 4-a to 4-b.

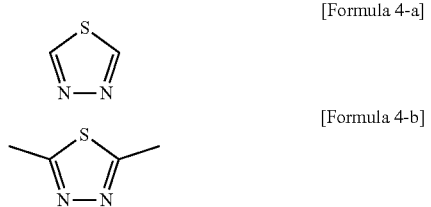

[Formula 4-a]

[Formula 4-b]

In a specific exemplary embodiment, among the curing accelerators, the pyrrole-based curing accelerator is one or more of the following formulas 5-a to 5-c.

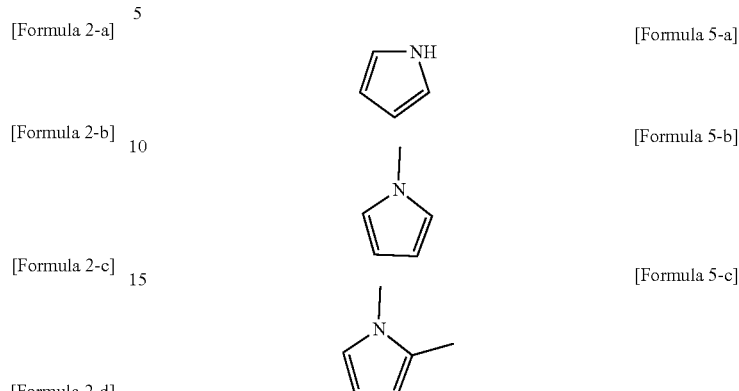

[Formula 5-a]

[Formula 5-b]

[Formula 5-c]

In an exemplary embodiment, the content of the curing accelerator is in the range of 0.01 to 10 parts by weight based on the total 100 parts by weight of the gel polymer electrolyte composition.

In addition, the present invention provides a manufacturing method of a lithium secondary battery by applying the gel polymer electrolyte composition described above. In an exemplary embodiment, a manufacturing method of lithium secondary battery according to the present invention includes: injecting the above-described gel polymer electrolyte composition into a battery case in a state where an electrode assembly including a positive electrode, a negative electrode, and a separator disposed between the positive electrode and the negative electrode is stored in a battery case.

In an exemplary embodiment, the manufacturing method of lithium secondary battery further includes: performing thermal crosslinking in the range of 10 minutes to 50 minutes after injecting the gel polymer electrolyte composition into the battery case.

In a specific exemplary embodiment, performing thermal crosslinking is performed in a temperature range of 55 to 80° C.

In another specific exemplary embodiment, the manufacturing method according to the present invention further includes: wetting of waiting for 1 minute to 30 hours between injecting the gel polymer electrolyte composition into the battery case and performing thermal crosslinking.

In another specific exemplary embodiment, the manufacturing method according to the present invention further includes: any one or more among an activation and a degassing after performing thermal crosslinking.

In addition, the present invention provides a secondary battery manufactured by the method described above. In an exemplary embodiment, a lithium secondary battery according to the present invention includes: an electrode assembly comprising a positive electrode, a negative electrode, and a separator disposed between the positive electrode and the negative electrode; a battery case accommodating and sealing the electrode assembly; and the gel polymer electrolyte composition injected into a battery case in which an electrode assembly is accommodated. The gel polymer electrolyte composition is as described above.

In a specific exemplary embodiment, the lithium secondary battery is a pouch-type battery.

Advantageous Effects

The present invention can increase the efficiency of the manufacturing process for a secondary battery using a thermally crosslinkable gel polymer electrolyte and improve the quality of manufactured products.

BRIEF DESCRIPTION OF THE DRAWINGS

FIG. 1 is a schematic diagram showing a leakage evaluation process for a pouch-type secondary battery according to an exemplary embodiment of the present invention.

BEST MODE FOR CARRYING OUT THE INVENTION

Hereinafter, the present invention will be described in detail. Prior to this, terms or words used in this specification and claims should not be construed as being limited to ordinary or dictionary meanings, and should be interpreted as a meaning and a concept consistent with the technical spirit of the present invention based on the principle that the inventor can appropriately define the concept of the terms in order to explain his/her invention in the best way.

The present invention provides a gel polymer electrolyte composition. In an exemplary embodiment, a gel polymer electrolyte composition according to the present invention includes: an oligomer represented by Formula 1 below; a curing accelerator that is a monocyclic or a polycyclic amine compound; a polymerization initiator; a non-aqueous solvent; and a lithium salt.

In the present invention, 'monocyclic' includes a case in which a single cyclic structure is included in the structural formula. 'Polycyclic' refers to a case in which two or more, specifically, two to four cyclic structures are included in the structural formula, and two or more cyclic structures include cases in which they are fused or complexed with each other.

In the present invention, the gelation rate of the electrolyte is remarkably increased by adding a curing accelerator that promotes the crosslinking reaction of the oligomer.

As an example, the oligomer may be a polypropylene carbonate (PPC)-based oligomer. In an exemplary embodiment, the oligomer is represented by Formula 1 below.

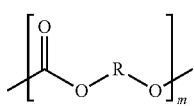

[Formula 1]

In Formula 1, R is an alkylene having carbon numbers 1 to 5 substituted with an alkyl group having carbon numbers 1 to 5, and m is an integer from 1 to 50.

Specifically, R is an alkylene having carbon numbers 1 to 3, more specifically, an alkylene having carbon number 2 with a methyl group substituted. The m is an integer of 1 to 10, an integer of 2 to 5, an integer of 2 to 3, or 2.

In an exemplary embodiment, in the present invention, the content of the oligomer is in the range of 0.1 to 30 parts by weight based on the total 100 parts by weight of the gel polymer electrolyte composition. More specifically, the content of the oligomer ranges from 1 to 10 parts by weight, 2 to 8 parts by weight, or 3 to 5 parts by weight. The content of the oligomer is within a range that does not degrade the performance of the secondary battery while preventing leakage of the electrolyte when applied to the secondary battery.

The gel polymer electrolyte composition may have a different curing temperature depending on the type of a polymerization initiator. In an exemplary embodiment, the gel polymer electrolyte composition is subjected to a crosslinking reaction under heat treatment conditions of 55 to 80° C., 60 to 75° C., or 68 to 75° C., and in this case, the curing time is in the range of 10 minutes to 50 minutes, 10 minutes to 40 minutes, or 20 to 40 minutes. In the gel polymer electrolyte composition, by using a curing accelerator, the curing time is reduced by 25% or more compared to that of the prior art.

In an exemplary embodiment, the curing accelerator includes one or more among a pyrimidine-based, an imidazole-based, a purine based, a thiadiazole-based, and a pyrrole based curing accelerators. The present invention includes the case of using one or a mixture of two or more of these curing accelerators.

In a specific exemplary embodiment, among the curing accelerators, the pyrimidine-based curing accelerator is one or more of the following formulas 1-a to 1-g.

[Formula 1-a]

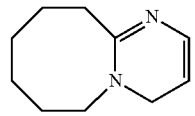

[Formula 1-b]

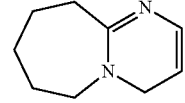

[Formula 1-c]

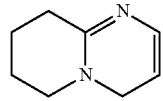

[Formula 1-d]

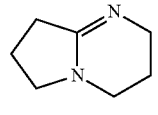

[Formula 1-e]

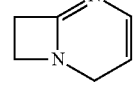

[Formula 1-f]

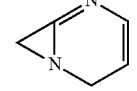

[Formula 1-g]

In a specific exemplary embodiment, among the curing accelerators, the imidazole-based curing accelerator is one or more of the following formulas 2-a to 2-i.

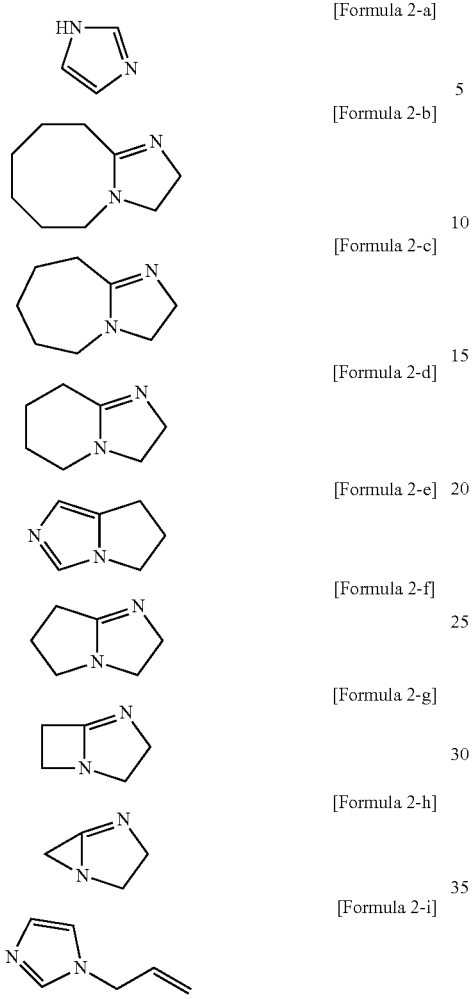

[Formula 2-a]

[Formula 2-b]

[Formula 2-c]

[Formula 2-d]

[Formula 2-e]

[Formula 2-f]

[Formula 2-g]

[Formula 2-h]

[Formula 2-i]

In a specific exemplary embodiment, among the curing accelerators, the purine-based curing accelerator is represented by the following formula 3-a.

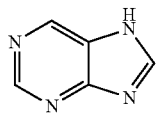

[Formula 3-a]

In a specific exemplary embodiment, among the curing accelerators, the thiadiazole-based curing accelerator is one or more of the following formulas 4-a to 4-b.

[Formula 4-a]

[Formula 4-b]

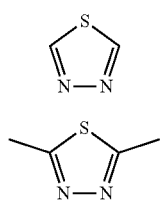

In a specific exemplary embodiment, among the curing accelerators, the pyrrole-based is curing accelerator one or more of the following formulas 5-a to 5-c.

[Formula 5-a]

[Formula 5-b]

[Formula 5-c]

In the present invention, the content of the curing accelerator is in the range of 0.01 to 10 parts by weight based on the total 100 parts by weight of the gel polymer electrolyte composition. Specifically, the content of the curing accelerator ranges from 0.1 to 10 parts by weight, 0.01 to 5 parts by weight, 0.2 to 5 parts by weight, or 0.5 to 2 parts by weight. The content of these curing accelerators is within a range capable of sufficiently reducing the curing rate while minimizing the input amount.

In addition, the present invention provides a manufacturing method of a lithium secondary battery to which the gel polymer electrolyte described above is applied. In an exemplary embodiment, the manufacturing method of a lithium secondary battery according to the present invention includes injecting the gel polymer electrolyte composition into a battery case in a state where an electrode assembly including a positive electrode, a negative electrode, and a separator disposed between the positive electrode and the negative electrode is stored in a battery case.

In the present invention, a secondary battery is manufactured by injecting the above-described gel polymer electrolyte composition into a battery case in which an electrode assembly is accommodated. Then, a gelation of the gel polymer electrolyte composition is performed through a heat treatment. Specifically, the present invention includes performing thermal crosslinking in the range of 10 minutes to 50 minutes after injecting the gel polymer electrolyte composition into a battery case. Performing such thermal crosslinking is a process of curing by inducing a crosslinking reaction of the injected gel polymer electrolyte. The curing time ranges from 10 minutes to 50 minutes, from 10 minutes to 40 minutes, or from 20 to 40 minutes. The present invention has the effect of reducing the curing time by 25% or more compared to that of the prior art.

In addition, in performing the thermal crosslinking, the heat treatment temperature may vary depending on the type of polymerization initiator introduced. In the present invention, for example, a curing accelerator represented by Formula 2 described above may be used. In this case, performing the thermal crosslinking may be performed in a temperature range of 55 to 80° C., 60 to 75° C., or 68 to 75° C.

In another exemplary embodiment, the present invention includes wetting of waiting for 1 minute to 30 hours between injecting the gel polymer electrolyte composition into a battery case and performing thermal crosslinking.

In another exemplary embodiment, the present invention includes any one or more among an activation and a degassing after performing thermal crosslinking.

In addition, the present invention provides a secondary battery manufactured by the manufacturing method described above. In an exemplary embodiment, a secondary battery according to the present invention includes an electrode assembly including a positive electrode, one negative electrode, and a separator disposed between the positive electrode and the negative electrode; a battery case accommodating and sealing the electrode assembly; and a gel polymer electrolyte composition injected into a battery case in which the electrode assembly is accommodated. The gel polymer electrolyte composition is as described above.

Depending on the method of stacking the electrode assembly, electrode assembly can be classified into a jelly-roll type, which is a rolled type, and a stacked type, which sequentially stacks an electrode assembly. And, depending on the shape of the battery case, the secondary battery can be divided into a cylindrical battery and a prismatic battery in which the electrode assembly is embedded in a cylindrical or prismatic metal can, and a pouch-type battery in which the electrode assembly is embedded in a pouch-type case of an aluminum laminate sheet. The secondary battery of the present invention may be a cylindrical, a prismatic or a pouch-type secondary battery, preferably a pouch-type secondary battery.

Meanwhile, the case may be made of a laminate sheet including a metal layer and a resin layer. Specifically, the laminate sheet may be an aluminum laminate sheet. The battery case of the laminate sheet may be composed of a lower case composed of an accommodating part with a sink-type structure and an outer part extending from the accommodating part, and an upper case coupled to the lower case by heat-sealing.

Hereinafter, the components of the secondary battery of the present invention will be described.

A positive electrode, one of the components of a secondary battery, has a structure in which a positive electrode active material layer is stacked on one or both surfaces of a positive electrode current collector. In one example, the positive electrode active material layer includes a positive electrode active material, a conductor, a binder polymer, and the like, and if necessary, may further include a positive electrode additive commonly used in the art.

The positive electrode active material may be a lithium-containing oxide, and may be the same or different. As the lithium-containing oxide, a lithium-containing transition metal oxide may be used.

For example, lithium-containing transition metal oxides may be one or a mixture of two or more selected from the group consisting of $Li_xCoO_2$ (0.5<x<1.3), $Li_xNiO_2$ (0.5<x<1.3), $Li_xMnO_2$ (0.5<x<1.3), $Li_xMn_2O_4$ (0.5<x<1.3), $Li_x(Ni_aCo_bMn_c)O_2$ (0.5<x<1.3, 0<a<1, 0<b<1, 0<c<1, a+b+c=1), $Li_xNi_{1-y}Co_yO_2$ (0.5<x<1.3, 0<y<1), $Li_xCo_{1-y}Mn_yO_2$ (0.5<x<1.3, 0<y<1), $Li_xNi_{1-y}Mn_yO_2$ (0.5<x<1.3, 0<y<1), $Li_x(Ni_aCo_bMn_c)O_4$ (0.5<x<1.3, 0<a<2, 0<b<2, 0<c<2, a+b+c=2), $Li_xMn_{2-z}Ni_zO_4$ (0.5<x<1.3, 0<z<2), $Li_xMn_{2-z}Co_zO_4$ (0.5<x<1.3, 0<z<2), $Li_xCoPO_4$ (0.5<x<1.3), and $Li_xFePO_4$ (0.5<x<1.3). In addition, the lithium-containing transition metal oxide may be coated with a metal such as aluminum (Al) or a metal oxide. In addition, besides the lithium-containing transition metal oxide, one or more of sulfide, selenide, and halide may be used.

The positive electrode active material may be included in the range of 94.0 to 98.5 wt % in the positive electrode active material layer. When the content of the positive electrode active material satisfies the above range, it is advantageous in terms of manufacturing a high capacity battery, and providing a sufficient positive electrode conductivity or an adhesive force between electrode materials.

The current collector used in the positive electrode is a metal with high conductivity, which can be easily adhered to the positive electrode active material slurry, and any one that is not reactive in the voltage range of an electrochemical device can be used. Specifically, non-limiting examples of the current collector for the positive electrode include a foil made of aluminum, nickel, or a combination thereof. The positive electrode active material layer further includes a conductor.

As the conductor, a carbon-based conductor is widely used, and it includes a sphere type or a needle type carbon-based conductive material. The sphere-type carbon-based conductor, in a mixed state with a binder, fills pores, which are empty spaces between active material particles, to improve physical contact between active materials, thereby reducing interface resistance and improving adhesive force between the lower positive electrode active material and the current collector.

The conductor may be included in an amount of 0.5 to 5 wt % in the positive electrode active material layer. When the content of the conductor satisfies the above range, there is an effect of providing sufficient positive electrode conductivity and lowering the interface resistance between the electrode current collector and the active material.

As the binder polymer, binders commonly used in the art may be used without limitation. For example, the binder may be a water-insoluble polymer that is soluble in organic solvents and insoluble in water, or a water-soluble polymer that is insoluble in organic solvents and soluble in water. Water-insoluble polymers may be one or more selected from the group consisting of polyvinylidene fluoride (PVDF), polyvinylidene chloride (PVDC), polyacrylonitrile (PAN), polypropylene oxide (PPO), polyethylene oxide-propylene oxide copolymer (PEO-PPO), polytetrafluoroethylene (PTFE), polyimide (PI), polyetherimide (PEI), styrene butadiene rubber (SBR), polyacrylate, and derivatives thereof.

The water-soluble polymer may be one or more selected from the group that includes various cellulose derivatives such as carboxymethylcellulose (CMC), methylcellulose (MC), cellulose acetate phthalate (CAP), hydroxypropylmethylcellulose (HPMC), and hydroxypropylmethylcellulose phthalate (HPMCP), etc.

The content of the binder polymer is proportional to the content of the conductor included in the upper positive electrode active material layer and the lower positive electrode active material layer. This is to provide an adhesive force to the conductor having a relatively very small particle size compared to the active materials. And this is because more binder polymers are required when the content of the conductor increases, and less binder polymers can be used when the content of the conductor decreases.

The negative electrode has a structure in which a negative electrode active material layer is stacked on one or both surfaces of a negative electrode current collector. In one example, the negative electrode active material layer includes a negative electrode active material, a conductor, a binder polymer, and the like, and may further include a negative electrode additive commonly used in the art, if necessary.

The negative electrode active material may include carbon material, lithium metal, silicon or tin, etc. When a carbon material is used as the negative electrode active material, both low crystalline carbon and high crystalline carbon may be used. Low crystalline carbons representatively include soft carbon and hard carbon, and high crystalline carbons representatively include high-temperature baked carbons such as natural graphite, kish graphite, pyrolytic carbon, mesophase pitch based carbon fiber, mesocarbon microbeads, mesophase pitches, petroleum or coal tar pitch derived cokes, etc.

Non-limiting examples of the current collector used for the negative electrode include a foil made of copper, gold, nickel, or a copper alloy or a combination thereof. In addition, the current collector may be used by stacking substrates made of the above materials.

In addition, the negative electrode may include a conductor and a binder commonly used in the related art.

The separator may be any porous substrate used in a lithium secondary battery, and for example, a polyolefin-based porous membrane or a non-woven fabric may be used, but is not particularly limited thereto.

Examples of the polyolefin-based porous membrane include polyethylenes such as high-density polyethylene, linear low-density polyethylene, low-density polyethylene, and ultra-high molecular weight polyethylene, and membranes formed of polyolefin-based polymers such as polypropylene, polybutylene, and polypentene, either alone or a polymer mixed with these.

In addition to polyolefin-based non-woven fabrics, the non-woven fabric includes, for example, non-woven fabrics formed of polyethyleneterephthalate, polybutyleneterephthalate, polyester, polyacetal, polyamide, polycarbonate, polyimide, polyetheretherketone, polyethersulfone, polyphenyleneoxide, polyphenylenesulfide, polyethylenenaphthalene, or the like either alone or a polymer mixed with these. The structure of the non-woven fabric may be a spun-bond non-woven fabric or a melt-blown non-woven fabric composed of long fibers.

The thickness of the porous substrate is not particularly limited, but may be 5 to 50 μm, and the pore size and the porosity present in the porous substrate are also not particularly limited, but may be 0.01 to 50 m and 10 to 95%, respectively.

Meanwhile, in order to improve the mechanical strength of the separator composed of the porous substrate and to suppress a short circuit between the positive electrode and the negative electrode, a porous coating layer containing inorganic particles and a binder polymer may be further included on at least one surface of the porous substrate.

The electrolyte may include an organic solvent and an electrolyte salt, and the electrolyte salt is a lithium salt. As the lithium salt, those commonly used in non-aqueous electrolytes for lithium secondary batteries may be used without limitation. For example, it contains Li+ as a cation, and contains one or more selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2$ as an anion.

As the organic solvent included in the above-described electrolyte, those commonly used in secondary battery electrolytes may be used without limitation, and for example, ether, ester, amide, linear carbonate, cyclic carbonate, etc. may be used alone or in combination of two or more. Among them, cyclic carbonates, linear carbonates, or carbonate compounds, which are mixtures of these, may be typically included.

Specific examples of the cyclic carbonate compound may be one or a mixture of two or more selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, vinyl ethylene carbonate, and halides thereof. As these halides, for example, there are fluoroethylenecarbonate (FEC), etc., but are not limited thereto.

In addition, specific examples of the linear carbonate compound may be one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof may be typically used, but are not limited thereto.

In particular, among the carbonate-based organic solvents, ethylene carbonate and propylene carbonate, which are cyclic carbonates, are high-viscosity organic solvents and have high permittivity to better dissociate lithium salts in the electrolyte. And when low-viscosity, low-dielectric-constant linear carbonates such as dimethyl carbonate and diethyl carbonate are mixed to such cyclic carbonates in an appropriate ratio, an electrolyte with higher electrical conductivity can be made.

In addition, as the ether in the organic solvent, any one selected from the group consisting of dimethyl ether, diethyl ether, dipropyl ether, methyl ethyl ether, methylpropyl ether and ethylpropyl ether, or a mixture of two or more thereof may be used, but is not limited thereto.

Moreover, as the esters in the organic solvents, esters include any one selected from the group consisting of methyl acetate, ethyl acetate, propyl acetate, methyl propionate, ethyl propionate, propyl propionate, γ-butyrolactone, γ-valerolactone, γ-caprolactone, α-valerolactone, and β-caprolactone, or a mixture of two or more thereof, but is not limited thereto.

The electrode assembly may be a lamination/stack type structure in which unit cells are stacked with a separator interposed therebetween or a stack/folding type structure in which unit cells are wound by a separating sheet.

In the electrode assembly, an electrode active material is applied to the positive and negative current collectors to form a mixture layer. Then, a positive electrode and a negative electrode in which pin holes are formed on an electrode tab and an electrode plate are manufactured through a notching device, and the positive electrode and the negative electrode are manufactured by bonding them to a separator that does not contain a pin hole. The type of the separator is not limited, but it may be organic/inorganic composite porous Safety-Reinforcing Separators (SRS).

Specifically, the SRS separator is manufactured by using inorganic particles and a binder polymer as active layer components on a polyolefin-based separator substrate. Here, it has a pore structure as well as a uniform pore structure formed by an interstitial volume between inorganic particles, which are active layer components. In the case of using such an organic/inorganic composite porous separator, it has the advantage of being able to suppress the increase in the thickness of the battery due to swelling during the formation process compared to the case of using a conventional separator. In the case of using a polymer capable of gelation during liquid electrolyte impregnation as a binder polymer component, it can also be used as an electrolyte at the same time. In addition, since the organic/inorganic composite porous separator can exhibit excellent adhesion characteristics by adjusting the contents of inorganic particles and binder polymers, which are components of the active layer in the separator, the battery assembly process can be easily performed.

Hereinafter, the present invention will be described in more detail through examples and the like. Since the present invention can have various changes and various forms, specific embodiments are exemplified and described in detail in the text. However, it should be understood that this is not intended to limit the present invention to the specific disclosed form, and includes all modifications, equivalents, and substitutes included in the spirit and scope of the present invention.

Example 1

LiPF$_6$ as a lithium salt was dissolved in a solvent in which ethylene carbonate (EC) and ethylmethyl carbonate (EMC) were mixed at a volume ratio of 3:7 at a concentration of 1M, and a gel polymer electrolyte composition was prepared by adding additives for each content based on the total weight of the gel polymer electrolyte as shown in Table 1 below.

Specifically, an oligomer was added in an amount of 4 wt %, and the structural formula of the oligomer is in Formula 1, where R is an alkylene having carbon number 2 with a methyl group substituted, and m is an integer ranging from 2 to 3.

A curing accelerator was added in an amount of 1 wt %, and the structural formula of the curing accelerator is shown in the following formula 1-c.

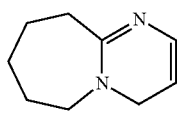

[Formula1-c]

As the polymerization initiator, V-59 product, an azo-based initiator manufactured by FUJIFILM WAKO Co., which is a thermal initiator, was used in an amount of 1 wt %.

As a positive electrode active material, LiNi$_{0.5}$Mn$_{1.5}$O$_4$ having a particle size of 5 μm was prepared, which was mixed with a carbon-based conductor and polyvinylidene fluoride as a binder in N-methylpyrrolidone (NMP) in a weight ratio of 94:3:3 to form a slurry, which was casted on a thin aluminum plate, dried in a vacuum oven at 120° C., and then rolled to prepare a positive electrode.

Separately, a negative electrode active material in which artificial graphite and silicon oxide (SiO$_2$) were mixed in a weight ratio of 9:1 was prepared, and 97 parts by weight of a negative electrode active material and 3 parts by weight of styrene butadiene rubber (SBR) were mixed in water to form a slurry, which was casted on a thin copper plate, dried in a vacuum oven at 130° C., and then rolled to prepare a negative electrode.

A separator made of 18 μm polypropylene was interposed between the positive and negative electrodes obtained above, inserted into a case, and then the prepared gel polymer electrolyte composition was injected. Then, a pouch-type lithium secondary battery was prepared through a curing time of 30 minutes at 65° C.

Examples 2 to 6

The curing accelerator was added in an amount of 1 wt %, and a gel polymer electrolyte composition was prepared in the same manner as in Example 1, except that the following formulas 2-e, 2-i, 3-a, 4-b, and 5-c were applied to the structural formula of the curing accelerator, respectively.

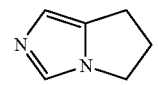

[Formula 2-e]

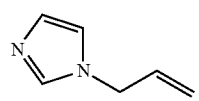

[Formula 2-i]

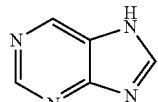

[Formula 3-a]

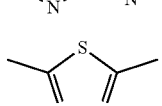

[Formula 4-b]

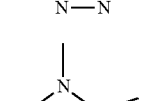

[Formula 5-c]

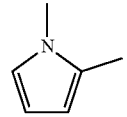

A lithium secondary battery was prepared in the same manner as in Example 1 using the prepared gel polymer electrolyte composition.

Comparative Example 1

An electrolyte composition was prepared by dissolving LiPF$_6$ as a lithium salt in a solvent in which ethylene carbonate (EC) and ethylmethyl carbonate (EMC) were mixed in a volume ratio of 3:7 at a concentration of 1M.

As a positive electrode active material, LiNi$_{0.5}$Mn$_{1.5}$O$_4$ having a particle size of 5 μm was prepared, which was mixed with a carbon-based conductor and polyvinylidene fluoride as a binder in N-methylpyrrolidone (NMP) in a weight ratio of 94:3:3 to form a slurry, which was casted on a thin aluminum plate, dried in a vacuum oven at 120° C., and then rolled to prepare a positive electrode.

Separately, a negative electrode active material in which artificial graphite and silicon oxide (SiO$_2$) were mixed in a weight ratio of 9:1 was prepared, and 97 parts by weight of a negative electrode active material and 3 parts by weight of styrene butadiene rubber (SBR) were mixed in water to form a slurry, which was casted on a thin copper plate, dried in a vacuum oven at 130° C., and then rolled to prepare a negative electrode.

A pouch-type lithium secondary battery was prepared by interposing a separator made of 18 μm polypropylene on the obtained positive electrode and negative electrode, inserting it into a case, and then injecting the prepared electrolyte composition.

Comparative Example 2

LiPF$_6$ as a lithium salt was dissolved in a solvent in which ethylene carbonate (EC) and ethylmethyl carbonate (EMC) were mixed at a volume ratio of 3:7 at a concentration of 1M, and a gel polymer electrolyte composition was prepared by adding additives for each content based on the total weight of the gel polymer electrolyte as shown in Table 1 below.

Lithium secondary battery was prepared in the same manner as in Example 1 using the prepared gel polymer electrolyte composition, but the curing time was set to 30 minutes.

Comparative Example 3

$LiPF_6$ as a lithium salt was dissolved in a solvent in which ethylene carbonate (EC) and ethylmethyl carbonate (EMC) were mixed at a volume ratio of 3:7 at a concentration of 1M, and a gel polymer electrolyte composition was prepared by adding additives for each content based on the total weight of the gel polymer electrolyte as shown in Table 1 below.

Lithium secondary battery was prepared in the same manner as in Example 1 using the prepared gel polymer electrolyte composition, but the curing time was set to 100 minutes.

Comparative Example 4

$LiPF_6$ as a lithium salt was dissolved in a solvent in which ethylene carbonate (EC) and ethylmethyl carbonate (EMC) were mixed at a volume ratio of 3:7 at a concentration of 1M, and a gel polymer electrolyte composition was prepared by adding additives for each content based on the total weight of the gel polymer electrolyte as shown in Table 1 below.

Lithium secondary battery was prepared in the same manner as in Example 1 using the prepared gel polymer electrolyte composition, but the curing time was set to 300 minutes.

Experimental Example: Evaluation of Leakage

Electrolyte leakage was evaluated for each of the secondary batteries manufactured in Examples 1 to 4 and Comparative Examples 1 to 3. Each secondary battery was a 100 Ah class large-sized cell.

The evaluation process is shown in FIG. 1. Referring to FIG. 1, each pouch-type secondary battery 100 is a 100 Ah class large-sized battery cell. The pouch-type secondary battery 100 has a structure in which an electrode assembly is accommodated in a pouch-type case. Based on the pouch-type case, a sealed area 120 was formed by heat-sealing four surfaces surrounding the electrode assembly accommodating part 110, and the electrode terminal 130 is drawn out on both sides. One side of the lower end of each pouch-type secondary battery 100 was incised as much as d (d=25 cm), and was stored for one week at room temperature conditions in a state in which it was tilted at an inclination angle of θ (θ=5°). Then, the amount of electrolyte leakage of each pouch-type secondary battery 100 was measured.

When it decreased by 3 wt % or more compared to the initial injection amount, it was determined that there was electrolyte leakage. The evaluation results were shown in Table 2 below.

TABLE 2

| Category | Whether electrolyte leakage occurred |
|---|---|
| Example 1 | X |
| Example 2 | X |
| Example 3 | X |
| Example 4 | X |
| Example 5 | X |
| Example 6 | X |

TABLE 1

| Category | Electrolyte | Oligomer content | Polymerization initiator content | Curing accelerator content | Curing accelerator type | Curing time |
|---|---|---|---|---|---|---|
| Example 1 | 1M $LiPF_6$ EC/EMC 3/7 | 4 wt % | 1 wt % | 1 wt % | Formula 1-c | 30 min |
| Example 2 | 1M $LiPF_6$ EC/EMC 3/7 | 4 wt % | 1 wt % | 1 wt % | Formula 2-e | 30 min |
| Example 3 | 1M $LiPF_6$ EC/EMC 3/7 | 4 wt % | 1 wt % | 1 wt % | Formula 2-i | 30 min |
| Example 4 | 1M $LiPF_6$ EC/EMC 3/7 | 4 wt % | 1 wt % | 1 wt % | Formula 3-a | 30 min |
| Example 5 | 1M $LiPF_6$ EC/EMC 3/7 | 4 wt % | 1 wt % | 1 wt % | Formula 4-b | 30 min |
| Example 6 | 1M $LiPF_6$ EC/EMC 3/7 | 4 wt % | 1 wt % | 1 wt % | Formula 5-c | 30 min |
| Comparative Example 1 | 1M $LiPF_6$ EC/EMC 3/7 | — | — | — | — | — |
| Comparative Example 2 | 1M $LiPF_6$ EC/EMC 3/7 | 4 wt % | 1 wt % | — | — | 30 min |
| Comparative Example 3 | 1M $LiPF_6$ EC/EMC 3/7 | 4 wt % | 1 wt % | — | — | 100 min |
| Comparative Example 4 | 1M LiPF6 EC/EMC 3/7 | 4 wt % | 1 wt % | — | — | 300 min |

TABLE 2-continued

| Category | Whether electrolyte leakage occurred |
|---|---|
| Comparative Example 1 | ◯ |
| Comparative Example 2 | ◯ |
| Comparative Example 3 | ◯ |
| Comparative Example 4 | X |

Referring to Table 2, in Examples 1 to 6, electrolyte leakage was not observed even when the curing time was 30 minutes. In contrast, in Comparative Example 1, gelation of the electrolyte was not done, and thus leakage was observed. Referring to Comparative Examples 2 and 3, it can be seen that in the case where the curing accelerator according to the present invention is not added, electrolyte leakage is observed under the condition of a curing time of 30 minutes or 100 minutes. Referring to Comparative Example 4, it can be seen that in the case where the curing accelerator is not added, no leakage was observed under the condition of a curing time of 300 minutes.

DESCRIPTION OF REFERENCE NUMERALS

100: POUCH-TYPE SECONDARY BATTERY
110: ELECTRODE ASSEMBLY ACCOMMODATING PART
120: SEALED AREA
130: ELECTRODE TERMINAL

The invention claimed is:

1. A gel polymer electrolyte composition, comprising:
an oligomer represented by Formula 1 below;
a curing accelerator that includes a monocyclic or a polycyclic amine compound;
a polymerization initiator;
a non-aqueous solvent; and
a lithium salt:

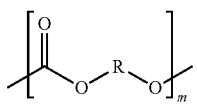

[Formula 1]

in the Formula 1,
R is an alkylene having 1 to 5 carbons substituted with an alkyl group having 1 to 5 carbons, and
m is an integer from 1 to 50.

2. The gel polymer electrolyte composition of claim 1, wherein
the gel polymer electrolyte composition has a curing time in a range of 10 minutes to 50 minutes under heat treatment conditions of 55 to 80° C.

3. The gel polymer electrolyte composition of claim 1, wherein a content of the oligomer is in a range of 0.1 to 30 parts by weight based on a total of 100 parts by weight of the gel polymer electrolyte composition.

4. The gel polymer electrolyte composition of claim 1, wherein the curing accelerator comprises one or more among a pyrimidine-based curing accelerator, an imidazole-based curing accelerator, a purine-based curing accelerator, a thiadiazole-based curing accelerator, and a pyrrole-based curing accelerator.

5. The gel polymer electrolyte composition of claim 4, wherein the pyrimidine-based curing accelerator includes one or more of the following formulas 1-a to 1-g:

[Formula 1-a]

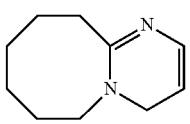

[Formula 1-b]

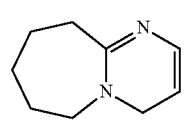

[Formula 1-c]

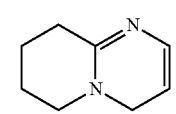

[Formula 1-d]

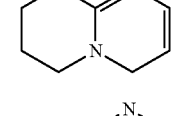

[Formula 1-e]

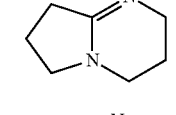

[Formula 1-f]

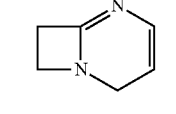

[Formula 1-g]

6. The gel polymer electrolyte composition of claim 4, wherein the imidazole-based curing accelerator includes one or more of the following formulas 2-a to 2-i:

[Formula 2-a]

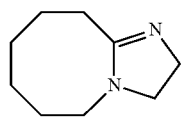

[Formula 2-b]

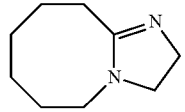

[Formula 2-c]

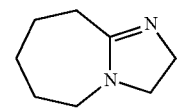

[Formula 2-d]

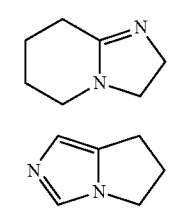

[Formula 2-e]

-continued

[Formula 2-f]

[Formula 2-g]

[Formula 2-h]

[Formula 2-i]

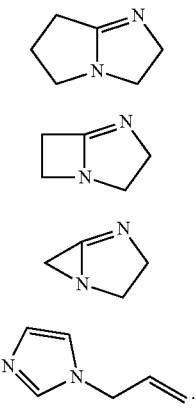

7. The gel polymer electrolyte composition of claim 4, wherein the purine-based curing accelerator includes a purine-based curing accelerator represented by the following formula 3-a:

[Formula 3-a]

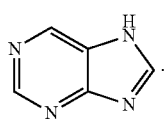

8. The gel polymer electrolyte composition of claim 4, wherein the thiadiazole-based curing accelerator includes one or more of the following formulas 4-a to 4-b:

[Formula 4-a]

[Formula 4-b]

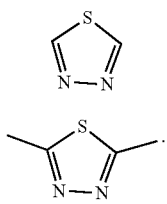

9. The gel polymer electrolyte composition of claim 4, wherein the pyrrole-based curing accelerator includes one or more of the following formulas 5-a to 5-c:

[Formula 5-a]

[Formula 5-b]

[Formula 5-c]

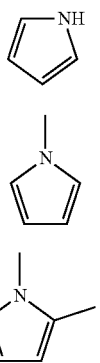

10. The gel polymer electrolyte composition of claim 1, wherein a content of the curing accelerator is in a range of 0.01 to 10 parts by weight based on a total of 100 parts by weight of the gel polymer electrolyte composition.

11. A manufacturing method of lithium secondary battery, comprising:
   injecting the gel polymer electrolyte composition according to claim 1 into a battery case comprising an electrode assembly including a positive electrode, a negative electrode, and a separator disposed between the positive electrode and the negative electrode, wherein the battery case stores the electrode assembly.

12. The manufacturing method of lithium secondary battery of claim 11, further comprising:
   performing thermal crosslinking in a range of 10 minutes to 50 minutes after the injecting of the gel polymer electrolyte composition into the battery case.

13. The manufacturing method of lithium secondary battery of claim 12, wherein the thermal crosslinking is performed in a temperature range of 55 to 80° C.

14. A lithium secondary battery, comprising:
   an electrode assembly comprising a positive electrode, a negative electrode, and a separator disposed between the positive electrode and the negative electrode;
   a battery case accommodating and sealing the electrode assembly; and
   the gel polymer electrolyte composition according to claim 1 in the battery case.

15. The lithium secondary battery of claim 14, wherein the lithium secondary battery is a pouch-type battery.

* * * * *